United States Patent [19]

Sakito

[11] 4,424,389
[45] Jan. 3, 1984

[54] SYNTHESIS OF 6-HYDROXYCHROMAN-2-METHANOL DERIVATIVES

[75] Inventor: Yoji Sakito, Ibaraki, Japan

[73] Assignee: Sumitomo Chemical Company, Limited, Osaka, Japan

[21] Appl. No.: 367,550

[22] Filed: Apr. 12, 1982

[30] Foreign Application Priority Data

Apr. 30, 1981 [JP] Japan .................................. 56-66681

[51] Int. Cl.³ .................. C07D 311/72; C07D 311/58
[52] U.S. Cl. .................................. 549/407; 549/411; 549/387; 548/324; 568/648; 568/436
[58] Field of Search ....................... 549/411, 407, 387; 568/648, 436; 548/324

[56] References Cited

U.S. PATENT DOCUMENTS

| | | | |
|---|---|---|---|
| 4,113,740 | 9/1978 | Cohen et al. | 549/453 |
| 4,151,177 | 4/1979 | Cohen et al. | 549/454 |
| 4,153,614 | 5/1979 | Barner et al. | 549/407 |
| 4,234,490 | 11/1980 | Barner et al. | 549/450 |
| 4,337,346 | 6/1982 | Mukaiyama et al. | 548/324 |

FOREIGN PATENT DOCUMENTS 11417  5/1980  European Pat. Off. ............ 548/324

OTHER PUBLICATIONS

Mayer et al., Helvetica Chimica ACTA 46, 650, (1963).
Scott et al., Helvetica Chimica ACTA 59, 290, (1976).
Cohen et al., Helvetica Chimica ACTA 61, 837, (1978).
Barner et al., Helvetica Chimica ACTA 62, 2384, (1979).
Cohen et al., J. Am. Chem. Soc. 101, 6710, (1979).
Mukaiyama et al., Chemistry Letters 705, (1979).

*Primary Examiner*—Nicky Chan
*Attorney, Agent, or Firm*—Stevens, Davis, Miller & Mosher

[57] ABSTRACT

A process for producing chroman, a compound of the formula,

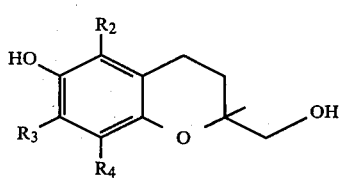

or an optically active compound thereof wherein $R_2$, $R_3$ and $R_4$ are each a hydrogen atom or a $C_1-C_4$ alkyl group, which comprises reacting a compound of the formula,

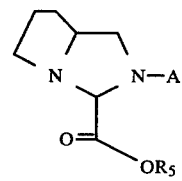

or an optically active compound thereof wherein A is an aryl group and $R_5$ is a $C_1-C_4$ alkyl group, with a compound of the formula,

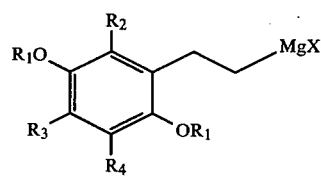

wherein $R_1$ is a $C_1-C_3$ alkyl group, X is a halogen atom and $R_2$, $R_3$ and $R_4$ are as defined above, to obtain a compound of the formula,

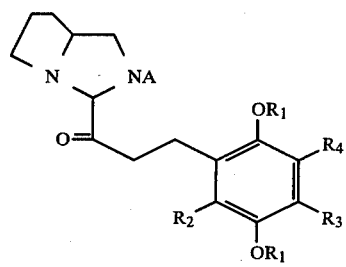

or an optically active compound thereof wherein A, $R_1$, $R_2$, $R_3$ and $R_4$ are as defined above, reacting the resulting compound with methylmagnesium halide and then hydrolyzing to obtain the corresponding 4-aryl substituted 2-hydroxy-2-methylbutanal, or an optically active compound thereof, reducing the resulting compound to obtain a diol, or an optically active compound thereof, and then oxidizing the resulting compound to obtain a compound of the formula,

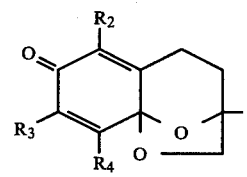

or an optically active compound thereof wherein $R_2$, $R_3$ and $R_4$ are as defined above, followed by reduction.

Chromans, the objective compounds of this invention, are an intermediate for the synthesis of tocopherols, particularly α-tocopherol.

17 Claims, No Drawings

SYNTHESIS OF 6-HYDROXYCHROMAN-2-METHANOL DERIVATIVES

The present invention relates to a method for the production of chromans. More particularly, it relates to a method for the production of chromans of the formula (7) (hereinafter, the term "chromans" means the compounds of this formula),

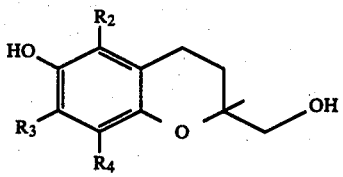

wherein $R_2$, $R_3$ and $R_4$ are each a hydrogen atom or a $C_1$–$C_4$ alkyl group, which comprises reacting a compound of the formula (1),

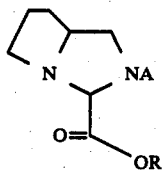

wherein A is an aryl group and $R_5$ is a $C_1$–$C_4$ alkyl group, with a compound of the formula (2),

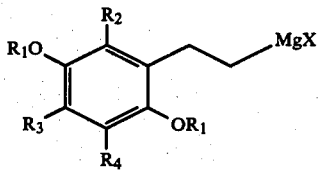

wherein $R_1$ is a $C_1$–$C_3$ alkyl group, X is a halogen atom and $R_2$, $R_3$ and $R_4$ are as defined above, to obtain a compound of the formula (3),

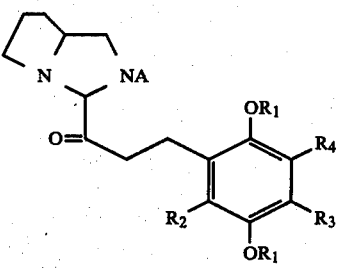

wherein A, $R_1$, $R_2$, $R_3$ and $R_4$ are as defined above, reacting the compound of the formula (3) with methylmagnesium halide and then hydrolyzing to obtain a compound of the formula (4),

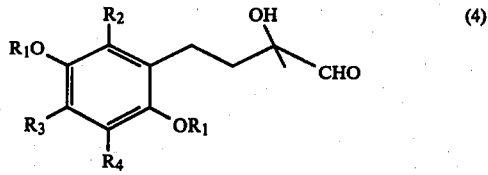

wherein $R_1$, $R_2$, $R_3$ and $R_4$ are as defined above, reducing the compound of the formula (4) to obtain a compound of the formula (5),

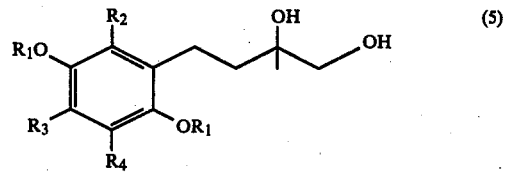

wherein $R_1$, $R_2$, $R_3$ and $R_4$ are as defined above, oxidizing the compound of the formula (5) to obtain a compound of the formula (6),

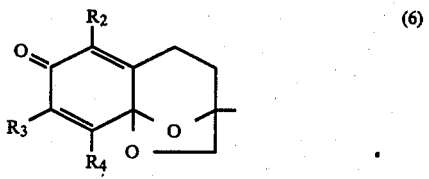

wherein $R_2$, $R_3$ and $R_4$ are as defined above, followed by reduction.

Chromans, the objective compounds of this invention, are an intermediate for the synthesis of tocopherols, particularly α-tocopherol.

α-Tocopherol has asymmetric carbon atoms at 2-, 4'- and 8'-positions as shown by the following formula:

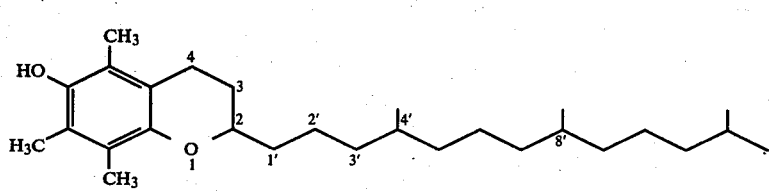

Therefore α-tocopherol has eight optical isomers and its titer of vitamin E activity varies with the kind of the optical isomers. For example, natural α-tocopherol (2R 4'R, 8'R) has a titer of 1.49 Iu/mg, while dl-α-tocopherpol (2RS, 4'RS, 8'RS) only 1.1 Iu/mg. For this reason, production of α-tocopherol of the same steric configuration as that of the natural one is of great significance. On the other hand, it is well known that both of the acetic acid esters of α-tocopherols having different steric configurations, (2RS, 4'R, 8'R) and (2RS, 4'RS, 8'RS), have a titer of 1 Iu/mg. This means that the vitamin E activity of α-tocopherol is not largely affected by the steric configuration of the 4'- and 8'-positions of the side chain, but mainly determined by the steric configuration at the 2-position. Consequently, a study has so far been made, taking into account the steric configuration at the 2-position, to produce intermediates for the synthesis of 2R-α-tocopherol. As methods to produce optically active intermediates, however, only optical resolution of various racemic intermediates is well known [Helv. Chim, Acta, 46, 650 (1963); ibid., 59, 290 (1976); ibid., 61, 837 (1978); ibid., 62, 2384 (1979); J. Am. Chem. Soc., 101, 6710 (1979)]. In such optical resolution, only 50% of the racemate is effectively used even by resolution of the highest efficiency, and the remaining 50% is useless, or, if not, additional steps are necessary to convert to compounds having a required steric configuration.

As a result of extensive study to overcome these drawbacks, the inventors found a novel method for the preduction of chromans. According to the present invention, the compound of the formula (4) in high optical purity is obtained by asymmetric synthesis, and optically active chromans can be produced from it without damaging the optical purity. According to the present invention, compounds alone having a required absolute steric configuration can be obtained selectively, and besides the asymmetric source can be recovered and re-used repeatedly.

The present invention, therefore, provides a method for producing optically active chromans in an industrially advantageous manner. Further, it is apparent that a method for producing racemic chromans using racemic compounds as material is also included in the scope of the present invention.

The compound of the formula (1) can be produced from N-(aryl-substituted aminomethyl)pyrrolidine and alkoxyhydroxyacetic acid ester [Japanese Patent Publication (Kokai) No. 162786/1980].

In the formula (1), A, an aryl group, includes unsubstituted and lower alkylsubstituted phenyl groups such as phenyl, p-tolyl, 2,6-xylyl groups etc., and of these, a phenyl group is preferable. $R_5$, a $C_1$–$C_4$ alkyl group, includes for example methyl, ethyl isopropyl, n-propyl, n-butyl groups etc.

The compound of the formula (1) is reacted with a Grignard reagent of the formula (2) to obtain the compound of the formula (3).

In the formula (2), $R_1$, a $C_1$–$C_3$ alkyl group, includes methyl, ethyl, n-propyl groups etc., and $R_2$, $R_3$ and $R_4$ each includes a hydrogen atom and $C_1$–$C_4$ alkyl groups such as methyl, ethyl, n-propyl, isopropyl, n-butyl groups etc., of which a hydrogen atom and a methyl group are preferred. A Grignard reagent of the formula (2) is obtained by reacting the corresponding halides (e.g. chlorides, bromides, iodides) with magnesium. As the solvent used in this reaction, those which are commonly used for Grignard reaction, for example tetrahydrofuran, ether and mixtures thereof, will do. Further, the yield of this reaction may be increased by adding magnesium halides (e.g. magnesium chloride, magnesium bromide, magnesium iodide) to the reaction system, and of these halides, magnesium chloride is preferred. The reaction can generally be effected at a temperature from the freezing point of the solvent to the boiling point of the solvent, but lower temperatures are desirable in order to decrease by-products.

The compound of the formula (3) thus obtained is reacted with methylmagnesium halide and then hydrolyzed to obtain the compound of the formula (4). Methylmagnesium halide referred to herein means methylmagnesium chloride, methylmagnesium bormide and methylmagnesium iodide. As a solvent used in this reaction, those which are commonly used for Grignard reaction, for example, ether, tetrahydrofuran and mixtures thereof, will do. The reaction can generally be effected at a temperature from the freezing point of the solvent to the boiling point of the solvent, but lower temperatures are desirable in order to produce optical isomers. Hydrolysis is carried out with acids such as hydrochloric acid, sulfuric acid etc. The reaction temperature may be raised if necessary, but this reaction will proceed smoothly even at room temperature.

The compound of the formula (4) thus obtained is reduced into the compound of the formula (5). As a reducing agent used in the reduction of said compound, common reducing agents capable of reducing a carbonyl group, for example metallic hydrides (e.g. lithium aluminum hydride, sodium borohydride, aluminum diisobutyl hydride, lithium borohydride) etc., will do. The solvent used in the reduction vaires with the kind of reducing agent, but those which are commonly used will do. For example, there are given ether, tetrahydrofuran etc. for reduction with lithium aluminum hydride or lithium borohydride; ethanol, diglyme etc. for reduction with sodium borohydride; and benzene, toluene, ether, tetrahydrofuran etc. for reduction with diisobutyl aluminum hydride. The reaction can generally be effected at a temperature from $-5°$ C. to the boiling point of the solvent.

The compound of the formula (5) thus obtained is then oxidized into the compound of the formula (6). In this reaction step, the compound of the formula (6) may be obtained directly by oxidation of the compound of the formula (5), but it may also be obtained by another route in which the compound of the formula (5) is once converted to the compound of the formula (8),

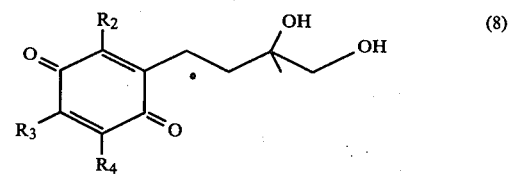

wherein $R_2$, $R_3$ and $R_4$ are as defined above, which is then converted to the compound of the formula (6) by ring-closure. As an oxidizing agent used in this reaction, there may be given those which are capable of oxidizing the ether form of hydroquinone into the quinone form thereof, for example ammonium ceric nitrate, ammonium ceric sulfate etc. The amount of oxidizing agent used is 1.0 to 1.3 equivalents, preferably 1.1 equivalents based on the compound (5). As the solvent used in this oxidation, when ammonium ceric nitrate or ammonium ceric sulfate is for example used as oxidizing agent, those which are commonly used together with said oxidizing agents will do. For example, mixture of water and acetonitrile, acetic acid or methanol and the like are used. The reaction temperature is not particularly limited, but it is preferably from $-10°$ C. to $30°$ C. Of the compounds of the formulae (6) and (8) thus obtained, the compound of the formula (8) can be converted to the compound of the formula (6) by reaction with an acid such as hydrochloric acid.

The compound of the formula (6) thus obtained is then reduced into the objective chromans represented by the formula (7). Reduction may be carried out by catalytic hydrogenation. As the catalyst for catalytic hydrogenation, there may be given catalysts having a reducing power such as palladium, platinum, nickel etc. As a solvent used in this reaction, those which are commonly used in catalytic hydrogenation will do, and for example, there may be given methanol, ethanol, acetic acid etc. The reaction temperature is not particularly limited. It may be raised if necessary, but this reaction will proceed smoothly at a temperature from −10° C. to 30° C.

The present invention will be illustrated specifically with reference to the following examples.

EXAMPLE 1

(1) A benzene solution containing 541 mg (3.14 mmole) of (S)-2-(anilinomethyl)pyrrolidine and 425 mg (3.45 mmole) of methyl hydroxymethoxyacetate was heated under reflux for 30 minutes while removing formed water azeotropically, to form 3-methoxycarbonyl-2-phenyl-hexahydro-1H-pyrrolo[1,2-c]imidazole. After removing the solvent from the resulting reaction solution, the residue was dissolved in 20 ml of tetrahydrofuran, and 330 mg (3.48 mmole) of anhydrous magnesium chloride was added thereto, followed by heating under reflux for 1 hour. The reaction solution was cooled to −100° C., and a solution of 2-(2,5-dimethoxy-3,4,6-trimethylphenyl) ethylmagnesium bormide in tetrahydrofuran was added dropwise thereto. Completion of the reaction was examined by thin layer chromatography. Thereafter, a saturated aqueous ammonium chloride solution and ether were added, and the organic layer was separated, dried over sodium sulfate and freed from the solvent by evaporation. The residue was purified on alumina column to obtain 730 mg (55%) of 3-[3-(2,5-dimethoxy-3,4,6-trimethylphenyl)propanoyl]-2-phenyl-hexahydro-1H-pyrrolo[1,2-c]imidazole.

nmr (CCl$_4$) δ (ppm)=1.6–3.7 (13H, m), 2.06 (9H, s), 3.50 (6H, s), 4.28 (1H, s), 6.25–7.16 (5H, m)

(2) 505 mg (1.20 mmole) of 3-[3-(2,5-dimethoxy-3,4,6-thimethylphenyl)propanoyl]-2-phenyl-hexahydro-1H-pyrrolo[1,2-c]imidazole obtained in (1) was dissolved in ether, and cooled to −100° C. To this solution was added about three equivalents of methylmagnesium iodide, and after 30 minutes, a saturated aqueous ammonium chloride solution was added. After separating the ether layer, 13 ml of 2% hydrochloric acid was added to the layer which was then stirred at 0° C. for 2 hours and extracted with ethyl acetate. The organic extract was washed with a saturated aqueous solution of sodium chloride dried over sodium sulfate and freed from the solvent by evaporation. The residue was purified on silica gel column to obtain 181 mg (54%) of (S)-4-(2,5-dimethoxy-3,4,6-trimethylphenyl)-2-hydroxy-2-methylbutanal.

nmr (CCl$_4$) δ (ppm)=1.20 (3H, s), 1.56–1.85 (2H, m), 2.05 (9H, s), 2.16–2.80 (2H, m), 3.40 (1H, s), 3.46 (3H, s), 3.51 (3H, s), 9.25 (1H, s)

[α]$_D$+39.6° (C. 0.53, benzene)

(3) 180 mg (0.643 mmole) of (S)-4-(2,5-dimethoxy-3,4,6-trimethylphenyl)-2-hydroxy-2-methylbutanal was dissolved in 5 ml of ethanol, and 30 mg (0.79 mmole) of sodium borohydride was added, followed by stirring at room temperature for 30 minutes. Water was added to the reaction solution which was then extracted with methylene chloride. The organic extract was washed with a saturated aqueous solution of sodium chloride dried over sodium sulfate and freed from the solvent under reduced pressure. The residue was purified on silica gel column to obtain 156 mg (86%) of (S)-4-(2,5-dimethoxy-3,4,6-trimethylphenyl)-2-methyl-1,2-butanediol.

mnr (CCl$_4$) δ (ppm)=1.17 (3H, s), 1.50 (2H, m), 2.08 (6H, s), 2.13 (3H, s), 2.67 (4H, m), 3.37 (2H, s), 3.55 (3H, s), 3.62 (3H, s), mp=83°–84° C.

[α]$_D$+3.1° (c 1.14, methylene chloride)

(4) 278 mg (0.986 mmole) of (S)-4-(2,5-dimethoxy-3,4,6-trimethylphenyl)-2-methyl-1,2-butanediol was dissolved in 4 ml of acetonitrile, and an aqueous solution (4 ml) containing 1.16 g (2.07 mmole) of ammonium ceric nitrate was added dropwise at room temperature for 2 minutes. After stirring for 5 minutes, the reaction solution was extracted with chloroform, and the chloroform extract was washed with a saturated aqueous solution of sodium chloride, dried over sodium sulfate and freed from the solvent under reduced pressure. The residue was purified on silica gel column to obtain 150 mg (65%) of (3S, 9aR)-3,6,8,9-tetramethyl-3,9a-epoxy-2,3,4,5,7,9a-hexahydro-1-benzoxepin-7-one and 50 mg (20%) of (S)-2-(3,4-dihydroxy-3-methylbutyl)-3,5,6-trimethyl-1,4-benzoquinone. Physical properties of (3S, 9aR)-3,6,8,9-tetramethyl-3,9a-epoxy-2,3,4,5,7,9a-hexahydro-1-benzoxepin-7-one nmr (CCl$_4$) δ (ppm)=1.35 (3H, s), 1.72 (3H, s), 1.80 (6H, s), 1.7–2.7 (4H, m), 3.48 (1H, d), 4.02 (1H, d)

mp=98°–99° C.

[α]$_D$−66.1° (c 0.039, benzene)

physical properties of (S)-2-(3,4-dihydroxy-3-methylbutyl)-3,5,6-trimethyl-1,4-benzoquinone nmr (CCl$_4$) δ (ppm)=1.23 (3H, s), 1.36–1.60 (2H, m), 2.00 (6H, s), 2.03 (3H, s), 2.40–2.73 (4H, s), 3.50 (2H, s)

(5)

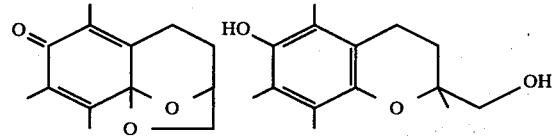

81 mg (0.35 mmole) of (3S, 9aR)-3,6,8,9-tetramethyl-3,9a-epoxy-2,3,4,5,7,9a-hexahydro-1-benzoxepin-7-one was dissolved in 8 ml of ethanol, and then catalytic hydrogenation was carried out at room temperature under atmospheric pressure with addition of 60 mg of 5% palladium/carbon. After removing the catalyst by filtration, the reaction solution was concentrated. The residue was purified on silica gel column to obtain 62 mg (76%) of S-6-hydroxy-2,5,7,8-tetramethyl-2-chromanmethanol.

nmr (CCl$_4$) δ (ppm )=1.36 (3H, s), 2.17 (6H, s), 2.20 (3H, s), 1.5–2.8 (5H, m), 3.63 (2H, brs), 4.43 (1H, s)

mp 127°–128° C.

[α]$_D$−2.8° (c 0.50, methylene chloride)

What is claimed is:

1. A process for producing a compound of the formula,

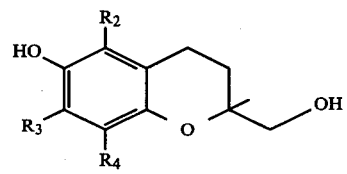

wherein $R_2$, $R_3$ and $R_4$ are each a hydrogen atom or a $C_1$–$C_4$ alkyl group, which comprises reducing a compound of the formula,

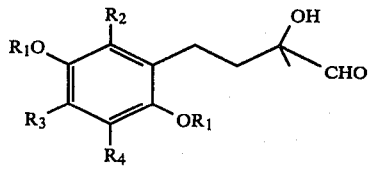

wherein $R_1$ is a $C_1$–$C_3$ alkyl group, and $R_2$, $R_3$ and $R_4$ are as defined above, to obtain a compound of the formula,

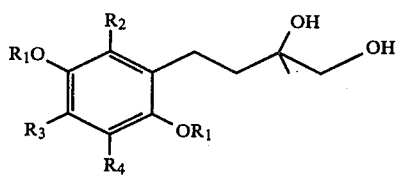

wherein $R_1$, $R_2$, $R_3$ and $R_4$ are as defined above, and oxidizing the resulting compound to obtain a compound of the formula,

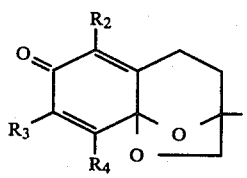

wherein $R_2$, $R_3$ and $R_4$ are as defined above, followed by reduction.

2. A process for producing an optically active compound of the formula,

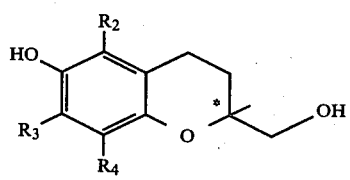

wherein $R_2$, $R_3$ and $R_4$ are each a hydrogen atom or a $C_1$–$C_4$ alkyl group, which comprises reducing an optically active compound of the formula,

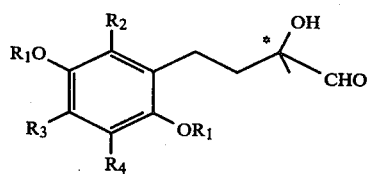

wherein $R_1$ is a $C_1$–$C_3$ alkyl group, and $R_2$, $R_3$ and $R_4$ are as defined above, to obtain an optically active compound of the formula,

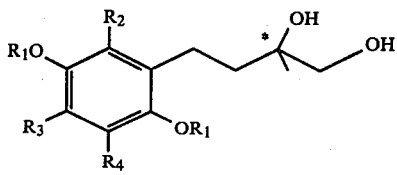

wherein $R_1$, $R_2$, $R_3$ and $R_4$ are as defined above, and oxidizing the resulting compound to obtain an optically active compound of the formula, wherein $R_2$, $R_3$ and $R_4$ are as defined above, followed by reduction.

3. A process according to claim 1 or 2, wherein $R_1$, $R_2$, $R_3$ and $R_4$ are each a methyl group.

4. A process according to claim 1 or 2 wherein a reducing agent used in the 1st-step reduction is metallic hydrides.

5. A process according to claim 1 or 2 wherein an oxidizing agent used in the oxidation step is ammonium ceric nitrate or ammonium ceric sulfate.

6. A process according to claim 5, wherein the amount of ammonium ceric nitrate or ammonium ceric sulfate is 1.0 to 1.3 equivalents based on the compound to be oxidized.

7. A process according to claim 1 or 2 wherein the final-step reduction is carried out by catalytic hydrogenation.

8. A process for producing a compound of the formula,

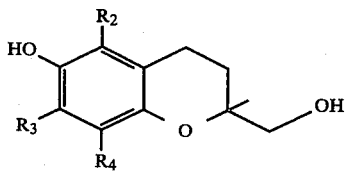

wherein $R_2$, $R_3$ and $R_4$ are each a hydrogen atom or a $C_1$–$C_4$ alkyl group, which comprises reacting a compound of the formula,

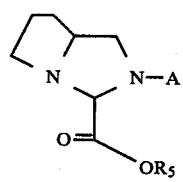

wherein A is an aryl group and $R_5$ is a $C_1$–$C_4$ alkyl group, with a compound of the formula,

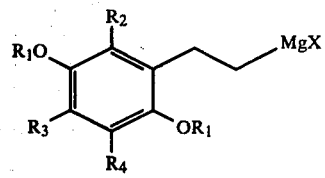

wherein $R_1$ is a $C_1$–$C_3$ alkyl group, X is a halogen atom and $R_2$, $R_3$ and $R_4$ are defined above, to obtain a compound of the formula,

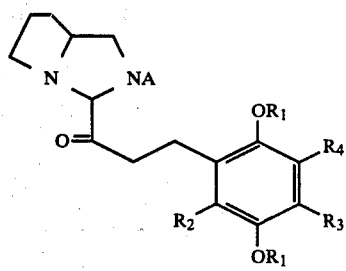

wherein A, $R_1$, $R_2$, $R_3$ and $R_4$ are as defined above, reacting the resulting compound with methylmagnesium halide and then hydrolyzing to obtain a compound of the formula,

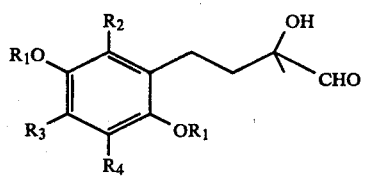

wherein $R_1$, $R_2$, $R_3$ and $R_4$ are as defined above, reducing the resulting compound to obtain a compound of the formula,

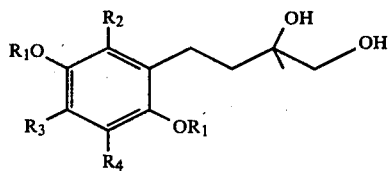

wherein $R_1$, $R_2$, $R_3$ and $R_4$ are as defined above, and then oxidizing the resulting compound to obtain a compound of the formula,

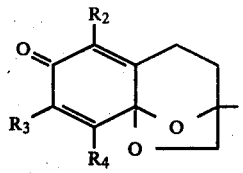

wherein $R_2$, $R_3$ and $R_4$ are as defined above, followed by reduction.

9. A process for producing an optically active compound of the formula,

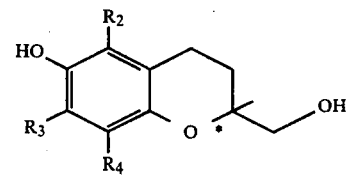

wherein $R_2$, $R_3$ and $R_4$ are each a hydrogen atom or a $C_1$–$C_4$ alkyl group, which comprises reacting an optically active compound of the formula,

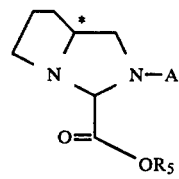

wherein A is an aryl group and $R_5$ is a $C_1$–$C_4$ alkyl group, with a compound of the formula,

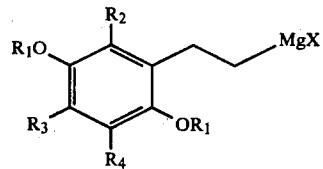

wherein $R_1$ is a $C_1$–$C_3$ alkyl group, X is a halogen atom and $R_2$, $R_3$ and $R_4$ are as defined above, to obtain an optically active compound of the formula,

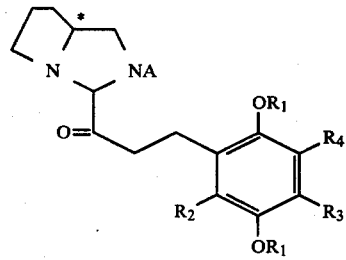

wherein A, $R_1$, $R_2$, $R_3$ and $R_4$ are as defined above, reacting the resulting compound with methylmagnesium halide and then hydrolyzing to obtain an optically active compound of the formula,

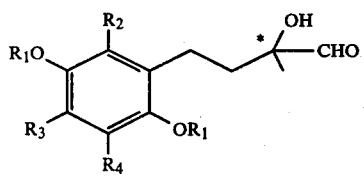

wherein $R_1$, $R_2$, $R_3$ and $R_4$ are as defined above, reducing the resulting compound to obtain an optically active compound of the formula,

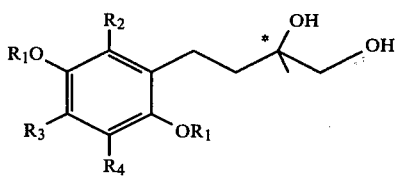

wherein $R_1$, $R_2$, $R_3$ and $R_4$ are as defined above, and then oxidizing the resulting compound to obtain an optically active compound of the formula,

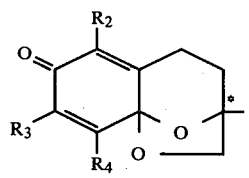

wherein $R_2$, $R_3$ and $R_4$ are as defined above, followed by reduction.

10. A process according to claim 8 or 9, wherein A is a phenyl group and $R_1$, $R_2$, $R_3$, $R_4$ and $R_5$ are each a methyl group.

11. A process according to claim 8 or 9 wherein X is a bromine atom.

12. A process according to claim 8 or 9 wherein methylmagnesium halide is methylmagnesium iodide.

13. A process according to claim 8 or 9 wherein an oxidizing agent used in the oxidation step is ammonium ceric nitrate or ammonium ceric sulfate.

14. A process according to claim 13, wherein the amount of ammonium ceric nitrate or ammonium ceric sulfate is 1.0 to 1.3 equivalents based on the compound to be oxidized.

15. A process according to claim 8 or 9 wherein the final-step reduction is carried out by catalytic hydrogenation.

16. A process according to claim 8 or 9 wherein magnesium halide is added as catalyst to the 1st-step reaction.

17. A process according to claim 16, wherein magnesium halide is magnesium chloride.

* * * * *

UNITED STATES PATENT AND TRADEMARK OFFICE
CERTIFICATE OF CORRECTION

PATENT NO. : 4,424,389

DATED : Jan. 3, 1984

INVENTOR(S) : Yoji Sakito, Ibaraki, Japan

It is certified that error appears in the above-identified patent and that said Letters Patent is hereby corrected as shown below:

On the title page

"Inventor: Yoji Sakito of Ibaraki, Japan" should read

-- Inventor: Yoji Sakito; Gohfu Suzukomo, both of Ibaraki, Japan --

UNITED STATES PATENT AND TRADEMARK OFFICE
CERTIFICATE OF CORRECTION

PATENT NO. : 4,424,389

DATED : Jan. 3, 1984

INVENTOR(S) : Yoji Sakito, Ibaraki, Japan

It is certified that error appears in the above-identified patent and that said Letters Patent is hereby corrected as shown below:

In the Specification:

Col. 2, lines 43-50 formula

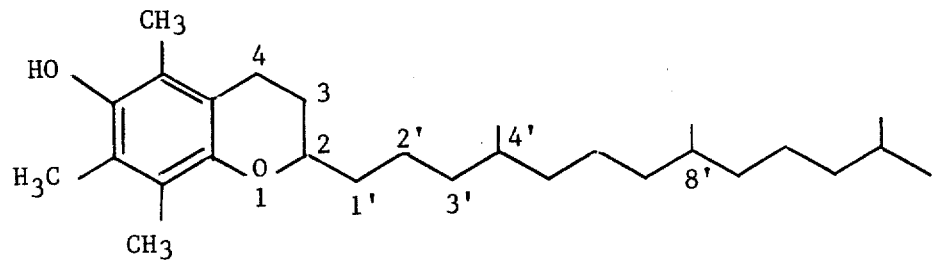

should read

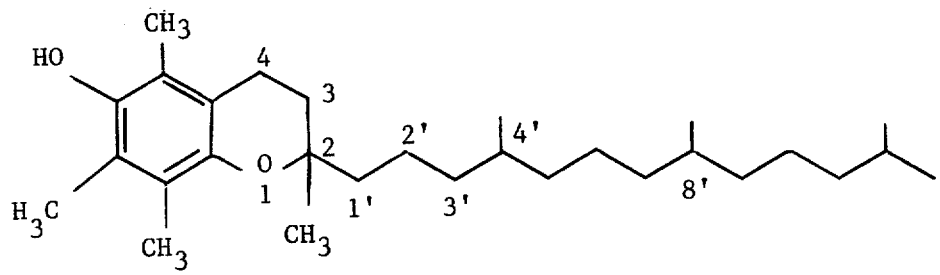

UNITED STATES PATENT AND TRADEMARK OFFICE
CERTIFICATE OF CORRECTION

PATENT NO. : 4,424,389
DATED : January 3, 1984
INVENTOR(S) : Yoji Sakito, Ibaraki, Japan It is certified that error appears in the above-identified patent and that said Letters Patent are hereby corrected as shown below:

Column 6, lines 35-41, left-hand formula reading:

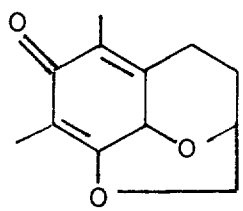

should read:

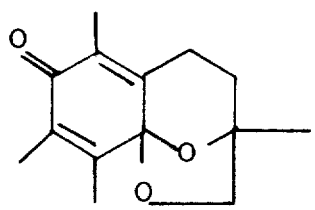

Signed and Sealed this

Eighteenth Day of June 1985

[SEAL]

Attest:

DONALD J. QUIGG

Attesting Officer     Acting Commissioner of Patents and Trademarks

UNITED STATES PATENT AND TRADEMARK OFFICE
CERTIFICATE OF CORRECTION

PATENT NO. : 4,424,389
DATED : January 3, 1984
INVENTOR(S) : Yoji SAKITO and Gohfu SUZUKAMO It is certified that error appears in the above-identified patent and that said Letters Patent is hereby corrected as shown below:

On the title page:

"Inventor: Yoji Sakito of Ibaraki, Japan" should read

-- Inventor: Yoji Sakito; Gohfu Suzukamo, both of Ibaraki, Japan --

This certificate supersedes Certificate of Correction issued June 18, 1985.

UNITED STATES PATENT AND TRADEMARK OFFICE
CERTIFICATE OF CORRECTION

PATENT NO. : 4,424,389
DATED : Jan. 3, 1984
INVENTOR(S) : Yoji Sakito et al

It is certified that error appears in the above-identified patent and that said Letters Patent is hereby corrected as shown below:

In the Specification:

Col. 2, lines 43-50 formula

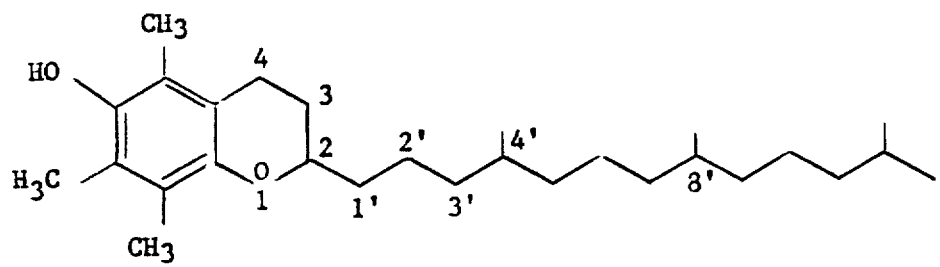

should read

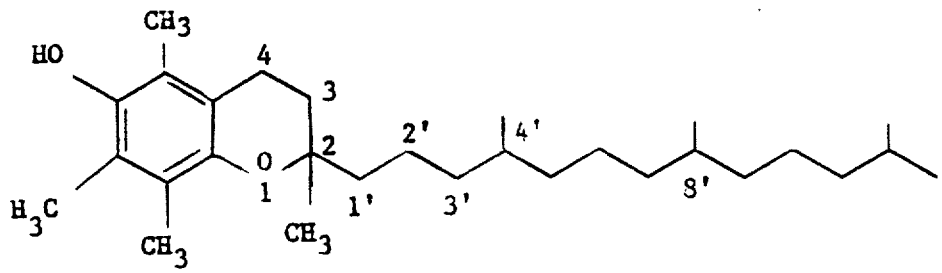

UNITED STATES PATENT AND TRADEMARK OFFICE
CERTIFICATE OF CORRECTION

PATENT NO. : 4,424,389

DATED : January 3, 1984

INVENTOR(S) : Yoji Sakito et al

It is certified that error appears in the above-identified patent and that said Letters Patent are hereby corrected as shown below:

Column 6, lines 35-41, left-hand formula reading:

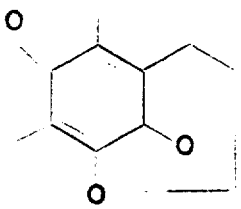

should read:

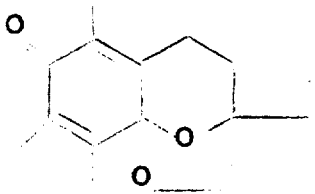

Signed and Sealed this

Twenty-third Day of February, 1988

Attest:

DONALD J. QUIGG

Attesting Officer

Commissioner of Patents and Trademarks